United States Patent
Shoji et al.

(10) Patent No.: US 8,017,379 B2
(45) Date of Patent: Sep. 13, 2011

(54) NUCLEIC ACID PURIFICATION INSTRUMENT

(75) Inventors: Yoshiyuki Shoji, Mito (JP); Shuhei Yamamoto, Mito (JP); Yoshihiro Yamashita, Hitahinaka (JP); Toshinari Sakurai, Hitahinaka (JP); Hiroshi Umetsu, Hitahinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 286 days.

(21) Appl. No.: 12/175,083

(22) Filed: Jul. 17, 2008

(65) Prior Publication Data

US 2009/0023904 A1     Jan. 22, 2009

(30) Foreign Application Priority Data

Jul. 18, 2007    (JP) ................. 2007-187361

(51) Int. Cl.
    *C12M 1/00*       (2006.01)
    *C07H 21/04*      (2006.01)
    *G01N 15/06*      (2006.01)
(52) U.S. Cl. ...... 435/283.1; 422/63; 422/68.1; 422/101; 536/23.1
(58) Field of Classification Search .................. None
See application file for complete search history.

(56) References Cited

U.S. PATENT DOCUMENTS

| | | | | |
|---|---|---|---|---|
| 6,117,398 A | * | 9/2000 | Bienhaus et al. | 422/101 |
| 6,159,368 A | * | 12/2000 | Moring et al. | 210/321.75 |
| 6,692,703 B2 | * | 2/2004 | Shoji et al. | 422/101 |
| 2005/0161377 A1 | * | 7/2005 | Fujimoto et al. | 210/120 |
| 2006/0011539 A1 | * | 1/2006 | Lee et al. | 210/613 |

FOREIGN PATENT DOCUMENTS

| | | |
|---|---|---|
| EP | 1 563 886 A1 | 1/2005 |
| JP | 2005-204578 | 8/2005 |
| JP | 2006-197851 | 8/2006 |
| WO | WO 2005/111210 | 11/2005 |
| WO | WO 2006/080580 | 8/2006 |

OTHER PUBLICATIONS

European Search Report issued in European Patent Application No. EP 08012938-2401 dated on Nov. 21, 2008.

* cited by examiner

*Primary Examiner* — Betty Forman
(74) *Attorney, Agent, or Firm* — McDermott Will & Emery LLP

(57) ABSTRACT

According to this invention, a nucleic acid purification instrument whereby it is possible to prevent dispersion of a mist thai causes contamination upon discharge of a solution is realized. A pressurizing nozzle is allowed to come into contact with a nucleic acid capturing column such that the sealing member is compressed. An aspiration fan is operated and thus the air in a closed channel flows toward the bottom part of a liquid receiving tank and then toward the aspiration fan as a result of a partition board. The inside of the nucleic acid capturing column is pressurized using tho pressurizing nozzle such that a solution in the nucleic acid capturing column is discharged and gravity-fed to the lower part of a liquid receiving tank. When the liquid volume m ihe nucleic acid capturing column becomes very small, the discharged solution is mixed with air so as to be formed into a mist and flows toward the aspiration fan and is captured by a protection filter so as not to bo discharged outside the closed channel.

12 Claims, 7 Drawing Sheets

NUCLEIC ACID PURIFICATION INSTRUMENT

BACKGROUND OF THE INVENTION

1. Field of the Invention

The present invention relates to a nucleic acid purification instrument for purifying nucleic acids from a sample containing nucleic acids.

2. Background Art

Analysis of nucleic acids, which are substances that carry genetic information, is being carried out in a wide variety of fields, such as academic research and medicine. Nucleic acid analysis methods often involve nucleic acid amplification techniques, typically polymerase chain reaction (PCR).

Herein, "PCR" refers to a method for amplifying nucleic acids in a nucleotide-sequence-specific manner, whereby a gene of interest can be detected or quantified in minute amounts. Upon nucleic acid analysis involving PCR or the like, nucleic acids isolated from a biological sample or the like are used. Upon nucleic acid purification, it is necessary to remove the influence of contaminants, including inhibitors of an analysis reaction, such as nucleic acids derived from the external environment that cause false-positive analytical results.

In one conventional method for nucleic acid purification from a biological sample, an operation such as ethanol precipitation or the like is carried out using poisonous material such as phenol or chloroform. In recent years, it has been common to use a method utilizing a property of nucleic acids whereby nucleic acids adsorb to a silica-containing solid phase or the like in the presence of a chaotropic agent as described in J. Clin. Microbiol., 28(3), 495-503 (1990) or a method utilizing a property of nucleic acids whereby nucleic acids adsorb to organic macromolecules such as acetylcellulose in the presence of a chaotropic agent and an aqueous organic solvent as described in JP Patent Publication (Kokai) No. 2005-204578 A.

The method described in JP Patent Publication (Kokai) No. 2005-204578 A is a method wherein a solution containing nucleic acids is introduced into a purification cartridge comprising, as nucleic-acid-adsorptive members, organic macromolecules such as acetylcellulose and the solution is discharged through the nucleic-acid-adsorptive members by pressurization, such that nucleic acids are allowed to adsorb to the nucleic-acid-adsorptive members. In such case, a pressure change in a nucleic acid purification column immediately after the discharge of the entire volume of a solution is analyzed, a pressure release valve is operated, and then the pressurized air in the nucleic acid purification column is released. Accordingly, dispersion of the discharged solution in a mist form caused by the remaining pressurized air is prevented such that the risk of causing contamination is reduced.

In addition, in the case of JP Patent Publication (Kokai) No. 2006-197851 A, a solution is discharged from a nucleic acid capturing column into a partitioned space such that the contamination caused by solutions discharged from a plurality of provided nucleic acid capturing columns is prevented.

SUMMARY OF THE INVENTION

As an aside, ideally, it is preferable that a solution in a nucleic acid capturing column in a nucleic acid purification instrument be completely discharged in all steps.

However, when the entire volume of a solution in a nucleic acid capturing column is discharged, the solution is continuously discharged while a certain volume thereof remains in the nucleic acid capturing column. Nevertheless, when the remaining volume becomes small, the solution is discharged in the form of a mixture of liquid and air. Eventually, the solution is obtained in a mist form.

The mist floats in the air and adheres to the outer circumference surface of a nucleic acid capturing column. When the nucleic acid capturing column is moved, the mist is separated from the column and adheres to another nucleic acid capturing column, a container, a reagent bottle, or the like, resulting in the probable generation of contamination.

There is a tendency to downsize instruments for nucleic acid purification treatment. As a result, a location at which a specimen is treated becomes close to another similar location, or a plurality of specimens are simultaneously treated. Accordingly, there will be increased risk of causing contamination.

In addition, in some cases, nucleic acids subjected to purification treatment are further subjected to amplification treatment in the subsequent step. In such cases, the above risks are further increased. For instance, it is possible to carry out an approximately one-billion-fold amplification (30 cycles) with the use of the aforementioned PCR amplification techniques, and thus dispersion of a minute volume of a mist generated from a sample containing nucleic acids significantly affects amplification results.

It is possible to prevent, to some extent, dispersion of a mist containing nucleic acids by a conventional technique. However, in such case, it is difficult to securely prevent such dispersion into the external environment.

It is an objective of the present invention to realize a nucleic acid purification method and a nucleic acid purification instrument whereby it is possible to prevent dispersion of a mist that causes contamination upon discharge of a solution.

In order to solve the above problems, the configuration of the present invention is described as follows: a nucleic acid purification method wherein nucleic acids of interest are purified from a liquid sample containing nucleic acids by pressurizing a liquid supplied to a nucleic acid capturing column having a nucleic-acid-adsorptive solid phase such that the liquid is allowed to pass through the nucleic-acid-adsorptive solid phase so as to be discharged from the nucleic acid capturing column, such method comprising the steps of:

connecting a liquid accommodating tank for accommodating the liquid discharged from the nucleic acid capturing column to a liquid discharge opening of the nucleic acid capturing column;

pressurizing the liquid supplied to the nucleic acid capturing column such that the liquid is allowed to pass through the nucleic-acid-adsorptive solid phase so as to be discharged from the nucleic acid capturing column;

capturing floating liquid components mixed with the air in the liquid accommodating tank so as to remove the liquid components floating with the air; and ventilating the air outside the liquid accommodating tank.

Effects of the Invention

According to the present invention, it is possible to realize a nucleic acid purification method and a nucleic acid purification instrument whereby it is possible to prevent dispersion of a mist that causes contamination upon discharge of a solution.

DESCRIPTION OF THE PREFERRED EMBODIMENTS

Hereinafter, embodiments of the present invention are described with reference to the drawings.

In addition, the embodiments described below are examples of the application of the nucleic acid purification method of the present invention to a nucleic acid purification instrument.

Figure 1:
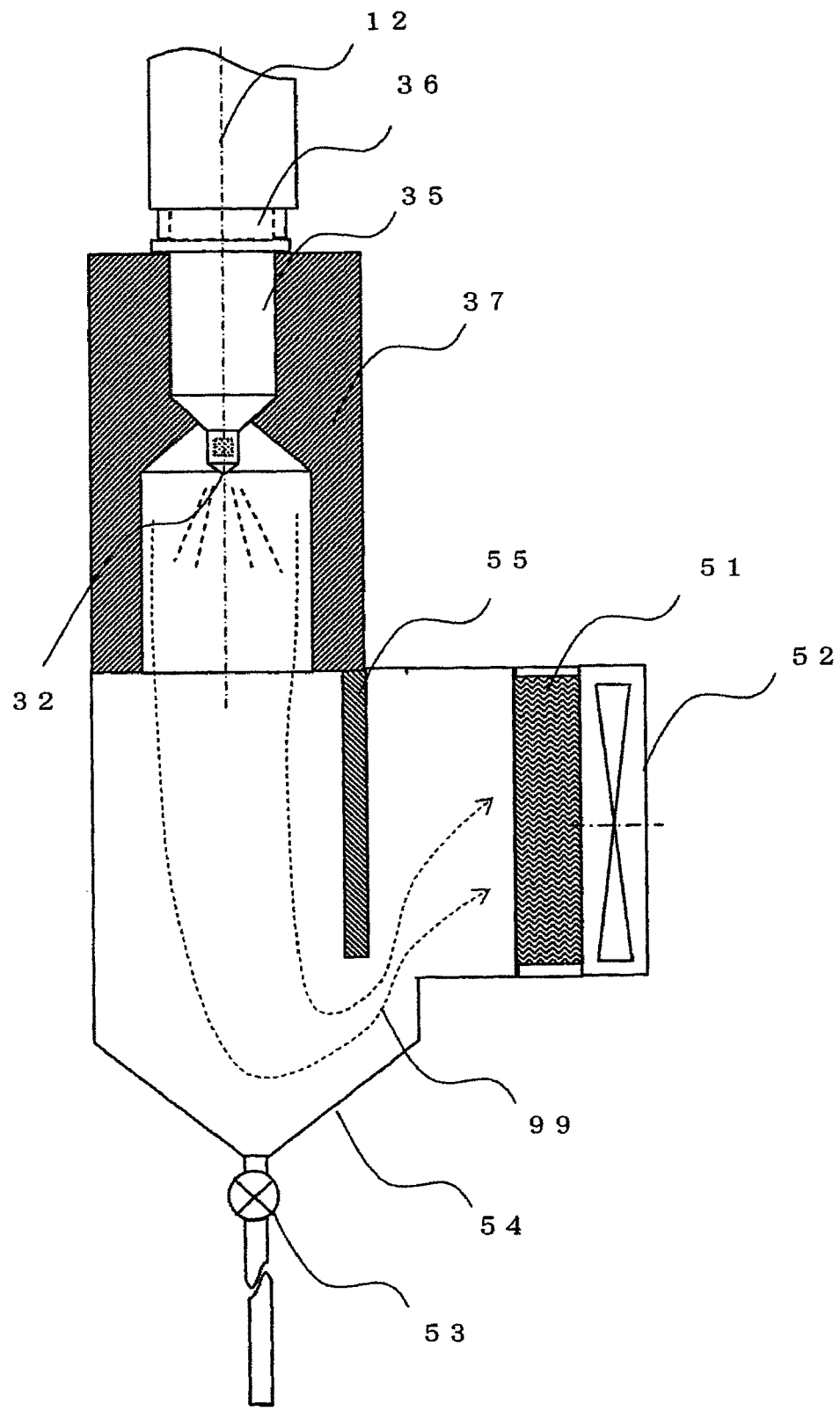
FIG. 1 shows a general structural diagram of a solution discharge channel in the first embodiment of the present invention.
Figure 2:
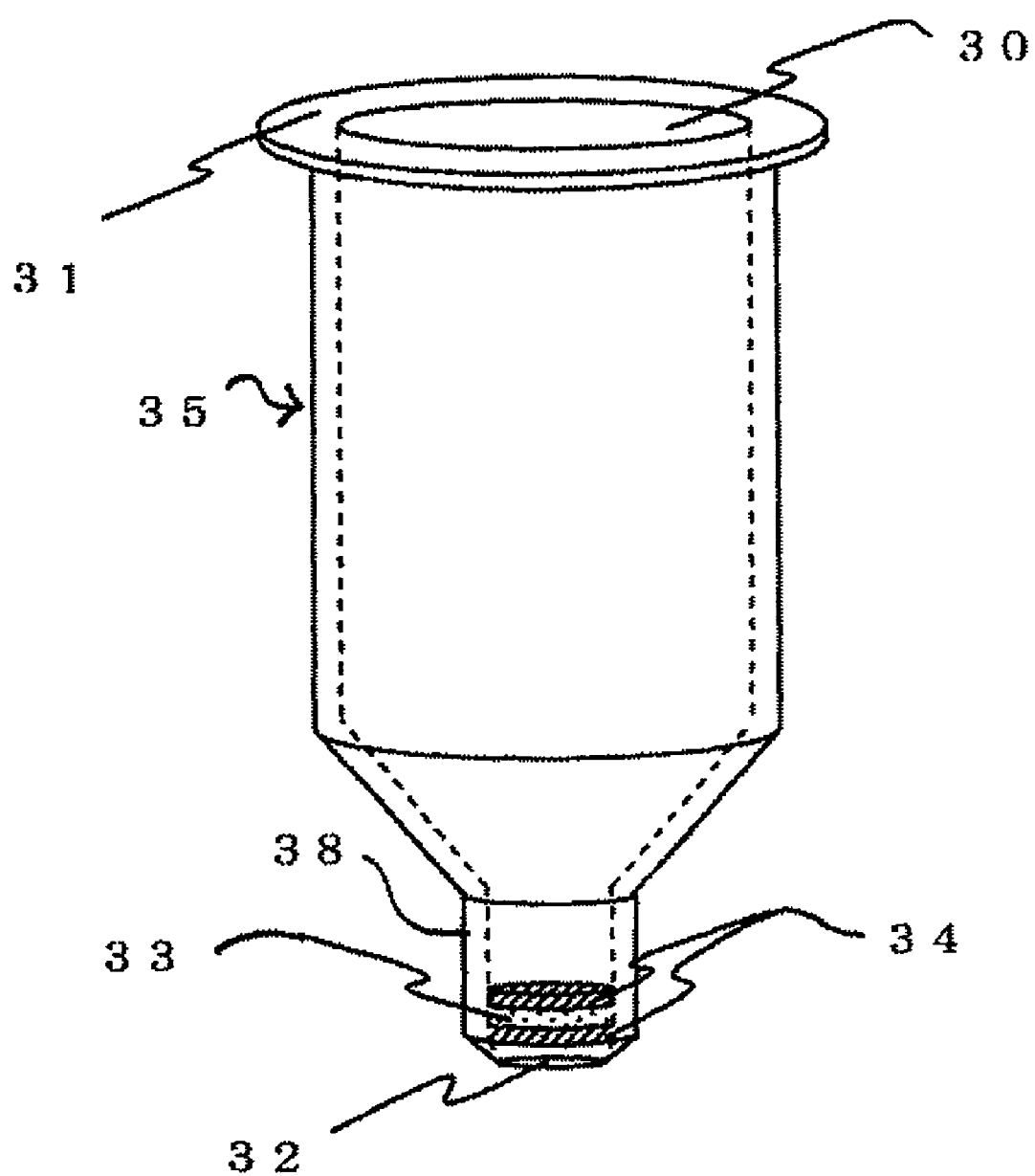
FIG. 2 shows a general structural diagram of a nucleic acid capturing column in the first embodiment of the present invention.
Figure 3:
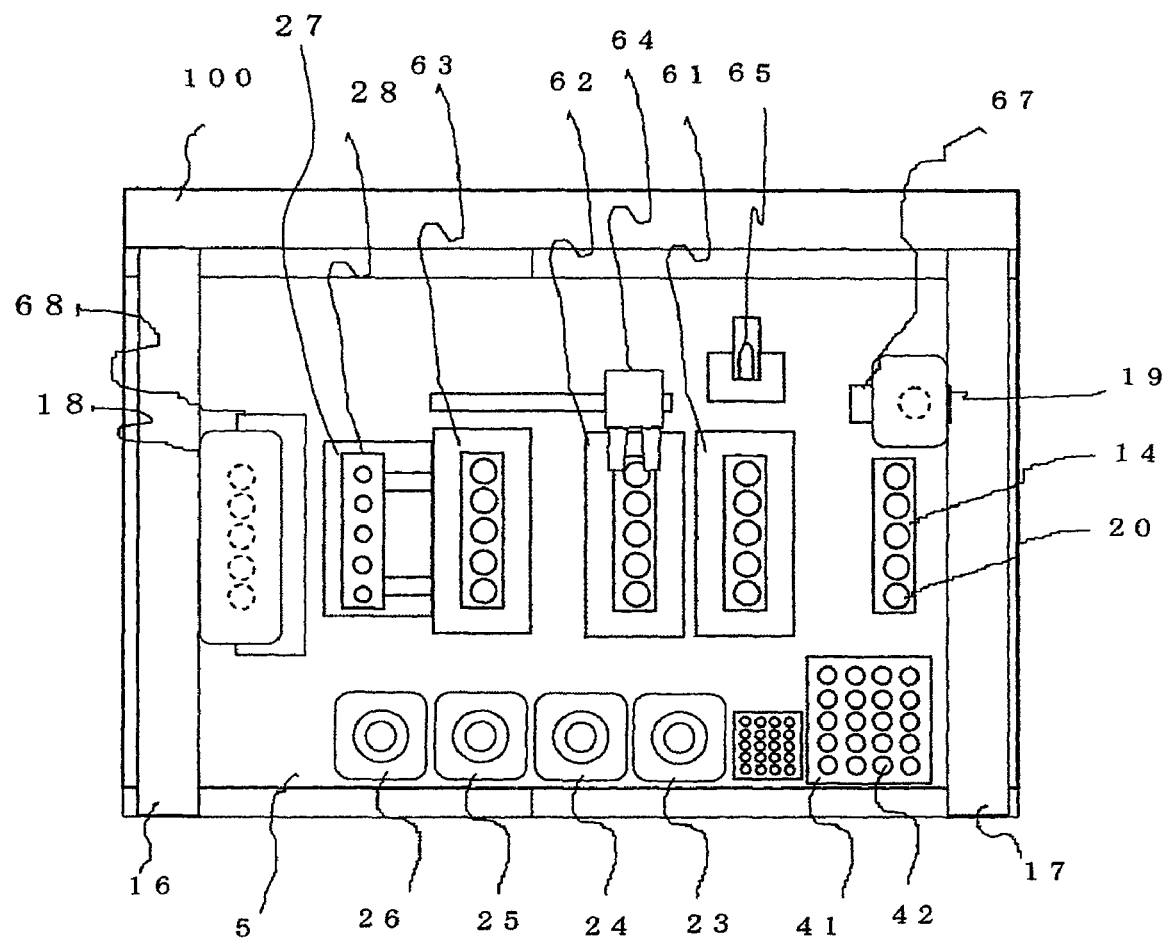
FIG. 3 shows a general structural plane view of a nucleic acid purification instrument to which the present invention is applied.
Figure 4:
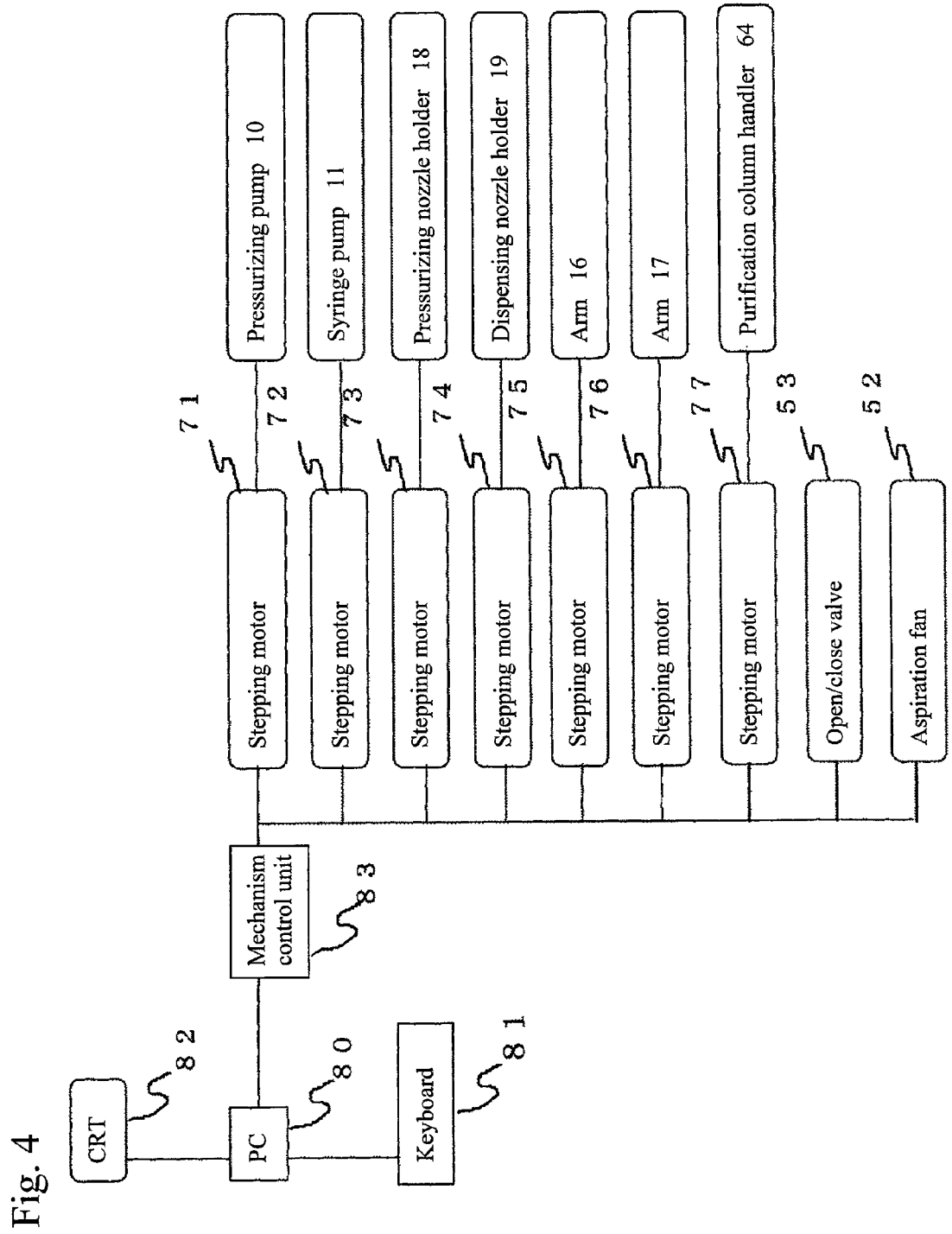
FIG. 4 shows a block diagram of an operation system of a nucleic acid purification instrument.
Figure 5:
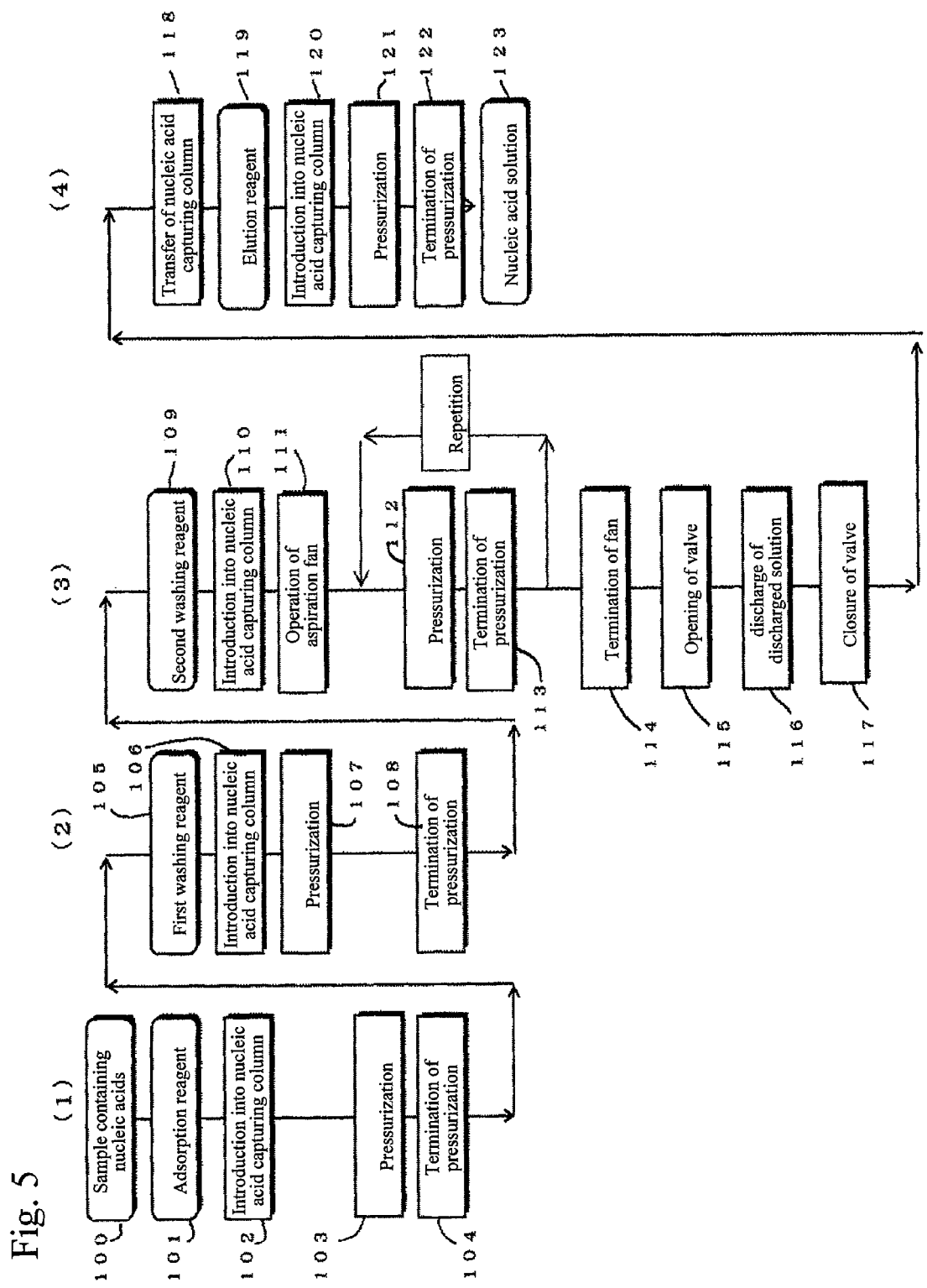
FIG. 5 shows an operational flowchart of the first embodiment of the present invention.

FIG. 1 shows a general structural diagram of a solution discharge channel in the first embodiment of the present invention. FIG. 2 shows a general structural diagram of a nucleic acid capturing column in the first embodiment of the present invention. FIG. 3 shows a general structural plane view of a nucleic acid purification instrument to which the present invention is applied. FIG. 4 shows a block diagram of an operation system of a nucleic acid purification instrument. FIG. 5 shows an operational flowchart of the first embodiment of the present invention.

In FIG. 1, a solution discharge channel in the first embodiment of the present invention is a closed channel. Such a closed channel is formed with a nucleic acid capturing column retention block 37, a liquid receiving tank 54, an open/close valve 53, a protection filter 51, and an aspiration fan 52 so as to result in a closed space surrounded by such components.

A nucleic acid capturing column retention block 37 is a pedestal on which a nucleic acid capturing column 35 is placed, such block being connected to the liquid receiving tank 54. The nucleic acid capturing column 35 is placed in a manner such that it is fitted into a continuous cylindrical hole formed on the nucleic acid capturing column retention block 37. Upon discharge of a solution, the nucleic acid capturing column 35 closely adheres to the nucleic acid capturing column retention block 37 via a pressurizing nozzle 12 shown in FIG. 4, which has been pushed downward so as to be in communication with a pressurizing pump 10, and a sealing member 36. Thus, a discharge channel is tightly connected with the nucleic acid capturing column 35.

The discharged liquid receiving tank 54 is located below the nucleic acid capturing column retention block 37 and functions to temporarily retain a liquid discharged via a discharge opening 32 of the nucleic acid capturing column 35. Preferably, the material of a discharged liquid receiving tank 54 is not affected by corrosion, deformation, dissolution, or the like caused by a discharged liquid. For instance, the material may be a metal such as stainless steel or a resin such as PP (polypropylene).

In addition, the open/close valve 53 is located at the lower part of the discharged liquid receiving tank 54 and functions to control the discharge of a discharged solution that has been temporarily retained in the discharged liquid receiving tank 54 into a discharged solution collection bottle (not shown). Preferably, such open/close valve 53 is a valve with which a channel can be arbitrarily opened and closed, such as a magnetic valve or a pinch cock, and is made of material such as fluoroplastics (Teflon (trademark)) that does not functionally deteriorate in the presence of liquid, as in the case of the discharged liquid receiving tank 54.

The protection filter 51 is provided in the closed channel and positioned further upstream in the channel than an aspiration unit described below. Such protection filter 51 captures a mist generated in the closed channel and functions to prevent dispersion of the mist discharged from the nucleic acid capturing column 35 outside the closed channel. In addition, in terms of required performance, the protection filter 51 preferably has ability equivalent to or exceeding the ability of an HEPA filter to capture, for example, particles having a particle size of 0.3 μm at a particle collection efficiency of 99.97% or higher.

An aspiration fan 52 aspirates the air in the closed channel and functions to guide the air to the protection filter 51. Such aspiration fan 52 is preferably a fan having increased aspiration power or air volume, such as a sirocco fan, in order to prevent a decrease in aspiration efficiency as a result of pressure loss caused by the protection filter 51.

Next, an operation for discharging liquid from the nucleic acid capturing column 35 in the first embodiment of the present invention is described. The operation is herein described by referring to a case in which the present invention is applied to a step of discharging a second washing reagent. Note that it is assumed that the nucleic acid capturing column 35 is positioned on a nucleic acid capturing column retention block 37 and contains a dispensed portion of the second washing reagent.

In order to discharge the second washing reagent in the nucleic acid capturing column 35, a pressurizing nozzle 12 connected with a pressurizing pump 10 (shown in FIG. 4 below) is lowered above the nucleic acid capturing column 35. A sealing member 36 is provided to the tip of the pressurizing nozzle 12 in a manner such that the nucleic acid capturing column 35 is securely connected with the pressurizing nozzle 12. The sealing member 36 is formed with an elastic resin, such as silicone rubber.

After the pressurizing nozzle 12 is allowed to come into contact with the nucleic acid capturing column 35, the pressurizing nozzle 12 is further lowered by a certain distance so that it closely adheres to the sealing member 36 in a manner such that the sealing member 36 is compressed. Then, an aspiration fan 52 is operated. As a result of the operation of the aspiration fan 52, the air in the closed channel flows toward the aspiration fan 52. In such case, the air flows along the internal wall of the closed channel. In the first embodiment of the present invention, a partition board 55 is provided in the closed channel. Such a partition board 55 is positioned so as to face the aspiration fan 52 in a manner such that the air discharged from the nucleic acid capturing column 35 flows toward the bottom part of a liquid receiving tank 54 and then flows toward the aspiration fan 52.

That is, as a result of installation of the partition board 55, the air in the closed channel flows from a discharge opening 32 of the nucleic acid capturing column 35 in a substantially vertically downward direction and then it turns and flows toward the aspiration fan 52, which is shown as an airflow 99 in FIG. 1.

In addition, a partition board 55 is not necessarily provided if the airflow (toward an aspiration fan 52 through a protection filter 51) passes vertically below the position of the aspiration fan 52 such that it is possible to allow a solution discharged from the nucleic acid capturing column 35 to flow in a vertically downward direction with respect to the discharge opening 32.

After the formation of such airflow, the pressurizing pump 10 is operated such that the inside of the nucleic acid capturing column 35 is pressurized. As a result, the pressure in the nucleic acid capturing column 35 is increased, resulting in the discharge of the second washing reagent. A solution that is discharged immediately after the initiation of the discharge of the second washing reagent is continuously discharged from the discharge opening 32 of the nucleic acid capturing column 35 so as to be gravity-fed to the lower part of a liquid receiving tank 54.

Meanwhile, when the liquid volume in the nucleic acid capturing column 35 becomes very small, the discharged solution is mixed with air so as to be formed into droplets. Eventually, such droplets form a mist. The solution exists in a mist form in the middle of an airflow formed by the aspiration fan 52, and the mist in such state (existing in the airflow) flows toward the aspiration fan 52. Then, the mist comprising the solution is captured by a protection filter 51 so as not to be discharged outside the closed channel.

After the termination of the discharge of the solution in the nucleic acid capturing column 35 into the closed channel, the operation of a pressurizing pump 10 and that of an aspiration fan 52 are terminated. Then, after the elapse of a certain period of time, the washing reagent in the closed channel is discharged into the discharge container.

As described above, it is possible to prevent dispersion of a mist formed with a solution that can cause contamination (such mist containing solution components floating in the air) outside a closed channel by constructing, as a ventilation unit used for nucleic acid purification, a liquid receiving tank that temporarily accommodates a discharged solution from a nucleic acid capturing column 35.

FIG. 2 shows an example of the nucleic acid capturing column 35 in the first embodiment of the present invention. The example thereof shown in FIG. 2 is a nucleic acid capturing column having a nucleic-acid-adsorptive solid phase.

In FIG. 2, the nucleic acid capturing column 35 comprises an opening 30 through which a solution such as a liquid sample containing nucleic acids, a washing reagent, or an elution reagent is introduced, a connecting portion 31 to which a pressurization mechanism is connected, and a tube 38 having a discharge opening 32 through which the solution is discharged. A nucleic-acid-adsorptive solid phase 33 is provided inside the tube 38, such solid phase being fixed with a supporting member 34.

An example of a nucleic-acid-adsorptive solid phase 33 that can be used is a solid phase comprising glass, silica, diatom earth, acetylcellulose, or the like. Such solid phase has a fine and tightly knitted filter-like structure having a plurality of consecutive liquid passage pores through which a solution can pass, such that a solution passes through the solid phase with sufficient efficiency of contact between the solution and the solid phase.

A supporting member 34 that can be used is a member capable of maintaining the shape and installation position of a nucleic-acid-adsorptive solid phase 33 and having a plurality of consecutive liquid passage pores through which a solution can pass. Examples thereof include sintered polypropylene particles.

The nucleic acid capturing column used is a nucleic acid capturing column 35 as shown in FIG. 2, such that the internal volume of the nucleic acid capturing column 35 is 2 ml, the material of the nucleic acid capturing column 35 is polypropylene, a nucleic-acid-adsorptive solid phase 33 is a glass fiber filter paper having an average pore size of 0.7 µm, and a supporting member 34 is a sintered body comprising polypropylene particles having an average particle retension size of approximately 100 µm.

The nucleic-acid-adsorptive solid phase 33 in the nucleic acid capturing column 35 has a fine and tightly knitted liquid passage pore structure. Thus, in a case of a highly viscous solution such as a liquid mixture of a sample and an adsorption solution, the liquid passage resistance becomes high. Therefore, in order to efficiently carry out liquid passage treatment, application of high pressure is necessary. However, when the passage of a solution has been achieved by applying high pressure, the residual pressure becomes high immediately after the discharge of the entire volume of the solution. Accordingly, dispersion of the discharged solution in a mist or droplet form might occur. Thus, it is necessary to avoid the risk of causing contamination.

Next, a general structure of a nucleic acid purification instrument 100 is described with reference to FIG. 3. In FIG. 3, a nucleic acid purification instrument 100 has two arms 16 and 17, which are movable in the horizontal direction (X direction). In the case of the arm 16, a pressurizing nozzle holder 18, which holds a pressurizing nozzle 12 that pressurizes liquid in a nucleic acid capturing column 35, is provided in a movable manner in the horizontal direction (Y direction) along the longitudinal direction of the arm 16.

Meanwhile, in the case of the other arm 17, a nozzle holder 19, which holds a dispensing nozzle (not shown), is provided in a movable manner in the horizontal direction (Y direction) along the longitudinal direction of the arm 17.

The pressurizing nozzle 12 and the dispensing nozzle can be operated in the vertical direction (Z direction) with respect to the arms 16 and 17, respectively. Each arm is provided at a different position at a different height because a horizontal movement area of the arm 16 and that of the arm 17 partially overlap each other.

A chip rack 41 carrying many unused dispensing chips 42 is set in a predetermined area on a working plane 5 on a base of a main body. Such chip rack 41 has holes through which dispensing chips 42 are inserted and held vertically. The chip rack 41 has a box shape such that it has a height to such an extent that the tip of each dispensing chip 42 does not come into contact with the working plane 5 or the bottom of the chip rack 41. A single chip rack 41 can hold 25 dispensing chips 42 at a maximum.

Further, a treatment block 61 is positioned on the working plane 5 and an unused treatment container 21 is preliminarily positioned on the treatment block 61. A specimen rack 14 that holds a plurality of specimen containers 20 each accommodating a specimen to be treated (namely, a sample containing nucleic acids) is set in a predetermined area. In this example, a specimen rack 14 can hold five specimen containers 20.

In addition, a purified product container rack 27 holding a plurality of unused purified product containers 28 is set in a predetermined area on the working plane 5. Each purified product container 28 is used for collecting a different liquid sample containing nucleic acids subjected to purification treatment. In this example, a container rack 27 can hold five purified product containers 28.

A chip remover 65 that removes a dispensing chip 42 connected to a reagent dispensing nozzle from the reagent dispensing nozzle is positioned on the working plane 5. The following are set on the relevant predetermined positions on the working plane 5: an adsorption reagent bottle 23 accommodating a solution containing an adsorption promoter that promotes nucleic acid adsorption to a nucleic-acid-adsorptive solid phase 33; a first washing reagent bottle 24 accommodating a washing reagent for washing a solid phase 33 in a nucleic acid capturing column 35; a second washing reagent bottle 25; and an elution reagent bottle 26 accommodating an elution reagent used for eluting nucleic acids adsorbing to a solid phase 33.

A pressurizing pump 10 that pressurizes the nucleic acid capturing column 35 and a syringe pump 11 (shown in FIG. 4) that aspirates and dispenses a specimen, an adsorption reagent, a first washing reagent, a second washing reagent, or an elution reagent are connected to a pressurizing nozzle 12 on an arm 16 and a reagent dispensing nozzle on an arm 17, respectively. Such pressurizing pump 10 discharges a solution in a nucleic acid capturing column 35. Such syringe pump 11 (shown in FIG. 4) carries out aspirating and discharging operations for each solution.

A dispensing chip 42 can be connected to a reagent dispensing nozzle by lowering the reagent dispensing nozzle above a chip rack 41 and allowing a dispensing chip 42 to be fitted into the tip of the nozzle. In addition, a chip remover 65 is used for removing a dispensing chip 42 connected to a reagent dispensing nozzle from the reagent dispensing nozzle. The dispensing chip 42 removed from the reagent dispensing nozzle falls into a chip disposal opening so as to be collected in a collection box (not shown). In addition, numerical references 62, 63, and 64 denote a waste liquid unit, an elution unit, and a nucleic acid capturing column handler, respectively. Numerical references 67 and 68 each denote a waiting position.

Next, the configuration of an electric system of the nucleic acid purification instrument 100 is described with reference to FIG. 4. In FIG. 4, the following examples are connected to a PC 80 serving as an operation control unit: a keyboard 81 serving as an operation panel for inputting operation conditions and specimen information; a CRT 82 serving as a display unit for displaying input information, warning information, and the like; and a mechanism control unit 83 that controls of mechanical components of the instrument.

A mechanism control unit 83 controls the operations of the following components: a stepping motor 71 for driving a piston that allows a pressurizing pump 10 to carry out an aspiration/discharge operation; a stepping motor 72 for driving a plunger that allows a syringe pump 11 to carry out an aspiration/discharge operation; a stepping motor 73 for moving a pressurizing nozzle holder 18 in the horizontal or vertical direction; a stepping motor 74 for moving a dispensing nozzle holder 19 in the horizontal or vertical direction; a stepping motor 75 for moving an arm 16 in the horizontal direction; a stepping motor 76 for moving an arm 17 in the horizontal direction; and a stepping motor 77 for operating a nucleic acid capturing column handler 63. Also, such a mechanism control unit 83 controls the operations of an open/close valve 53 and an aspiration fan 52. Each component of the nucleic acid purification instrument 100 is operated in accordance with a predetermined program.

Next, a series of purification steps involving the use of a nucleic acid purification instrument using the closed channel of the first embodiment of the present invention are described. FIG. 5 shows an operational flowchart of nucleic acid purification steps.

A nucleic acid purification method comprises the following steps:

(1): an adsorption step for introducing a liquid mixture obtained by adding an adsorption reagent to a sample containing nucleic acids into a nucleic acid capturing column and pressurizing the inside of the nucleic acid capturing column such that the liquid mixture is allowed to pass through a nucleic-acid-adsorptive solid phase so as to be discharged;

(2): a first washing step for introducing a first washing reagent into the nucleic acid capturing column and pressurizing the inside of the nucleic acid capturing column such that the washing reagent is allowed to pass through the nucleic-acid-adsorptive solid phase so as to be discharged;

(3): a second washing step for introducing a second washing reagent into the nucleic acid capturing column and pressurizing the inside of the nucleic acid capturing column such that the washing reagent is allowed to pass through the nucleic-acid-adsorptive solid phase so as to be discharged; and (4): an elution step for introducing an elution reagent into a nucleic acid capturing column, pressurizing the inside of the nucleic acid capturing column such that a washing reagent is allowed to pass through the nucleic-acid-adsorptive solid phase so as to be discharged, and obtaining a nucleic acid solution.

Examples of samples containing nucleic acids that can be used include body fluids such as whole blood, plasma, serum, urine, stool, saliva, sputum, or seminal fluid, tissues or cells of plants and animals, microorganisms, bacteria, viruses, and suspensions containing any thereof or lysates of any thereof.

Also, examples of adsorption reagents that can be used include a variety of chaotropic salts, which allow nucleic acids to be released in a sample containing nucleic acids and promote adsorption of nucleic acids to a nucleic-acid-adsorptive solid phase. Examples of such chaotropic salt that can be used include guanidine thiocyanate, guanidine hydrochloride, sodium iodide, potassium iodide, and sodium perchlorate. In addition, in order to promote release of nucleic acids, a surfactant, a protease, and the like can be used.

Preferred examples of surfactants that can be used include nonionic surfactants such as polyoxyethylene (10) octylphenyl ether and polyoxyethylene (20) sorbitan monolaurate. In addition, in order to deactivate a nucleotidase contained in a sample containing nucleic acids or derived from an external environment, reductants such as 2-mercaptoethanol and dithiothreitol and metal chelating agents such as ethylenediamine tetraacetate can be used. Further, in order to promote release of nucleic acids, heating, agitation, homogenization, and ultrasonication treatments can be used in combination. Furthermore, in order to promote adsorption of nucleic acids to a nucleic-acid-adsorptive solid phase, an organic solvent can be used.

Preferred examples of organic solvents that can be used include aqueous organic solvents such as methanol, ethanol, isopropanol, butanol, acetone, diethylene glycoldimethyl ether, and ethyl lactate.

Next, nucleic acid purification steps using a nucleic acid purification instrument are described in detail. A sample containing nucleic acids is introduced into a specimen container 20 and the container is held in a specimen rack 14. The specimen rack 14 is placed in a specimen placement position on an instrument 100. The chip rack 41 carrying dispensing chips 42, bottles 23, 24, 25, and 26, a treatment container 21, and a purified product container 28 are positioned at their predetermined places. Then, a nucleic acid purification operation is initiated using the purification instrument 100.

First, an arm 17 and a nozzle holder 19 located at a waiting position 67 are operated such that a dispensing nozzle is moved over the chip rack 41 and a first dispensing chip 42 is fitted into a dispensing nozzle. Then, the thus connected dispensing chip 42 is moved above the specimen rack 14 and lowered to the specimen container 20 of interest, following which a syringe pump 11 is allowed to carry out an aspiration operation such that a certain volume of the sample containing nucleic acids is aspirated in the dispensing chip 42.

Next, the dispensing chip 42 inside the specimen container 20 is elevated therefrom and a small volume of air is aspirated into the tip of the dispensing chip 42. Then, the dispensing nozzle is moved above a first treatment container 21 on a treatment block 61. Thereafter, the dispensing chip 42 is lowered into the specimen container 20 such that a certain volume of a specimen is discharged in the treatment container 21 as a result of a discharge operation of the syringe pump 11.

Then, the dispensing nozzle is moved to a chip remover 65 such that the dispensing chip 42 is removed from the dispensing nozzle. The removed dispensing chip 42 falls by itself into a used chip collection box (not shown) that is located below the chip remover 65 such that the chip is collected.

Then, the nozzle holder 19 is operated such that the dispensing nozzle is moved above the chip rack 41. A second dispensing chip 42 is fitted into the dispensing nozzle. The thus connected dispensing chip 42 is moved above an adsorption reagent bottle 23 and is lowered into the bottle 23. The syringe pump 11 is allowed to carry out an aspiration operation such that a certain volume of an adsorption reagent is aspirated into the dispensing chip 42.

Next, the dispensing chip 42 inside the adsorption reagent bottle 23 is elevated therefrom and a small volume of air is aspirated into the tip of the dispensing chip 42. Then, the dispensing nozzle is moved above a first treatment container 21 on a treatment block 61. Thereafter, the dispensing chip 42 is lowered into the treatment container 21 such that a certain volume of an adsorption reagent is discharged as a result of a discharge operation of the syringe pump 11.

After the discharge of the adsorption reagent, the entire volume of the adsorption reagent and that of the sample containing nucleic acids discharged in the treatment container 21 are re-aspirated into the same dispensing chip 42 and again discharged therefrom. Such aspiration/discharge operation is repeatedly carried out. Accordingly, the sample containing nucleic acids and the adsorption reagent are mixed with each other. Then, the entire volume of the mixed solution in the treatment container 21 is aspirated into the dispensing chip 42.

After the aspiration of the mixed solution into the dispensing chip 42, a small volume of air is aspirated into the tip of the dispensing chip 42, following which the dispensing chip 42 is moved to the position of a first nucleic acid capturing column 35 on a discharged liquid unit 62. Then, the tip of the dispensing chip 42 is lowered into the nucleic acid capturing column 35 and the entire volume of the mixed solution in the dispensing chip 42 is discharged. After the termination of the discharge, the dispensing nozzle is moved to the position of the chip remover 65 and the dispensing chip 42 is discarded.

Next, the pressurizing nozzle 12 connected to the arm 16 is moved above the nucleic acid capturing column 35 into which the solution obtained in the previous step has been discharged. Then, the pressurizing nozzle 35 is lowered so as to closely adhere to the nucleic acid capturing column 35 via a sealing member 36 provided to the tip of the lowered nozzle 35.

Then, the pressurizing pump 10 is operated such that the solution in the nucleic acid capturing column 35 is discharged. The mixed solution discharged from the nucleic acid capturing column 35 is temporarily accommodated in a liquid receiving tank 54. A discharged solution collection bottle (not shown) is connected to the lower part of the liquid receiving tank 54 via an open/close valve 53. When the open/close valve 53 is opened, the entire volume of the solution discharged through the nucleic acid capturing column 35 is collected in the discharged solution collection bottle.

After the discharge of the mixed solution of the adsorption reagent and the specimen in the nucleic acid capturing column 35, the pressurizing nozzle is elevated and temporarily moved to a waiting position 68.

The above operations correspond to steps 100 to 104 in FIG. 5.

Next, operations corresponding to steps 105 to 108 in FIG. 5 are described.

The arm 17 and the nozzle holder 19 located at the waiting position are operated such that the dispensing nozzle is moved above the chip rack 41 and a third dispensing chip is fitted into the dispensing nozzle 13. Then, the thus connected dispensing chip 42 is moved above the first washing reagent bottle 24 and is lowered into the bottle 24. Thereafter, a certain volume of the first washing reagent is aspirated into the dispensing chip 42 by allowing the syringe pump 11 to carry out an aspiration operation.

A first washing reagent is a solution capable of maintaining adsorption of nucleic acids to a nucleic-acid-adsorptive solid phase and removing nonspecific adsorbing substances such as proteins. Examples of a first washing reagent that can be used include a solution that can be used in an adsorption solution, such solution containing a chaotropic salt, a surfactant, a reductant, a metal chelating agent, an organic solvent, or the like.

Next, the dispensing chip 42 inside the first washing reagent bottle 23 is elevated therefrom and a small volume of air is aspirated into the tip of the dispensing chip 42. Subsequently, the dispensing nozzle is moved above the nucleic acid capturing column 35, the dispensing chip 42 is lowered into the nucleic acid capturing column 35, and a certain volume of the first washing reagent is discharged as a result of a discharge operation of the syringe pump 11. Thereafter, the dispensing nozzle is moved to the chip remover 65 and the dispensing chip 42 is removed from the dispensing nozzle.

Next, the pressurizing nozzle 12 connected to the arm 17 is moved above the nucleic acid capturing column 35 into which the solution obtained in the above step has been discharged. Then, the pressurizing nozzle 12 is lowered so as to closely adhere to the nucleic acid capturing column 35 via a sealing member 36 provided to the tip of the lowered pressurizing nozzle 12. Subsequently, the pressurizing pump 10 is operated such that the first washing reagent in the nucleic acid capturing column 35 is discharged. The first washing reagent discharged from the nucleic acid capturing column 35 is temporarily accommodated in a liquid receiving tank 54. Thereafter, the open/close valve 53 is opened such that the entire volume of the first washing reagent is collected in the discharged solution collection bottle 56. After the discharge of the first washing reagent in the nucleic acid capturing column 35, the pressurizing nozzle 12 is elevated and temporarily moved to the waiting position 68.

The above operations correspond to steps 105 to 108 in FIG. 5.

Next, operations corresponding to steps 109 to 117 in FIG. 5 are described.

The arm 17 and the nozzle holder 19 located at the waiting position are operated such that the dispensing nozzle is moved above the chip rack 41 and a fourth dispensing chip 42 is fitted into the dispensing nozzle. Then, the thus connected dispensing chip 42 is moved above the second washing reagent bottle 25 and is lowered into the bottle 25. Thereafter, a certain volume of the second washing reagent is aspirated into the dispensing chip 42 by allowing the syringe pump 11 to carry out an aspiration operation.

Next, the dispensing chip 42 inside the second washing reagent bottle 25 is elevated therefrom and a small volume of air is aspirated into the tip of the dispensing chip 42. Subsequently, the dispensing nozzle is moved above the nucleic acid capturing column 35, the dispensing chip 42 is lowered into the nucleic acid capturing column 35, and a certain volume of the second washing reagent is discharged into the nucleic acid capturing column 35 as a result of a discharge operation of the syringe pump 11.

A second washing reagent is a solution capable of maintaining adsorption of nucleic acids to a nucleic-acid-adsorptive solid phase 33 and removing nonspecific adsorbing substances, which were impossible to remove with a first washing reagent, and the remaining components of a first washing reagent to such an extent that the substances and the remaining components can be removed before an elution reagent is introduced in the subsequent step and thus they do not inhibit the subsequent analytical reaction. Examples of a second washing reagent that can be used include a solution containing, for example, a volatile organic solvent such as ethanol or acetone.

Next, the dispensing nozzle is moved above the chip remover 65 and the dispensing chip 42 is removed from the dispensing nozzle.

Next, the pressurizing nozzle 12 connected to the arm 16 is moved above the nucleic acid capturing column 35 into which the solution obtained in the previous step has been discharged. Then, the pressurizing nozzle 12 is lowered so as to closely adhere to the nucleic acid capturing column 35 via a sealing member 36 provided to the tip of the lowered nozzle 12. Thereafter, the aspiration fan 52 is operated such that the air in the vicinity of the discharge opening 32 of the nucleic acid capturing column 35 is aspirated so as to flow toward the aspiration fan 52.

Next, the pressurizing pump 10 is operated such that the solution and the second washing reagent in the nucleic acid capturing column 35 are discharged.

Thereafter, the pressurizing nozzle 12 is slightly elevated such that the pressurizing pump 10 is moved to the position at which pressurization is initiated. Then, the pressurizing nozzle 12 is lowered again so as to closely adhere to the nucleic acid capturing column 35. Next, the pressurizing pump 10 is operated and an operation for discharging the solution in the nucleic acid capturing column 35 is repeated.

The above discharge operation is repeated for a predetermined number of times (e.g., 10 times). Then, the pressurizing nozzle 12 is elevated and temporarily moved to the waiting position 68. After the completion of the discharge operation, the aspiration fan 52 is stopped such that the air stops flowing. After a period of waiting until the air stops flowing, the open/close valve 53 is opened such that the liquid in the discharged liquid receiving tank 54 is discharged. Then, the open/close valve 53 is closed.

The above operations correspond to steps 109 to 117 in FIG. 5.

Next, operations corresponding to steps 118 to 123 in FIG. 5 are described.

The nucleic acid capturing column 35 is moved from a discharged liquid unit 62 to an elution unit 63 with the use of a nucleic acid capturing column handler 64. Then, the arm 17 and the nozzle holder 19 located at the waiting position are operated such that the dispensing nozzle is moved above the chip rack 41 and a fifth dispensing chip 42 is fitted into the dispensing nozzle. Then, the thus connected dispensing chip 42 is moved above the elution reagent bottle 26 and is lowered into the bottle 26. Thereafter, a certain volume of the elution reagent is aspirated into the dispensing chip 42 by allowing the syringe pump 11 to carry out an aspiration operation.

Next, the dispensing chip 42 inside the elution reagent bottle 25 is elevated therefrom and a small volume of air is aspirated into the tip of the dispensing chip 42. Then, the dispensing nozzle is moved above the nucleic acid capturing column 35, the dispensing chip 42 is lowered into the nucleic acid capturing column 35, and a certain volume of the elution reagent is discharged as a result of a discharge operation of the syringe pump 11. An elution reagent is a solution that elutes nucleic acids from a nucleic-acid-adsorptive solid phase 33 and does not contain components that inhibit the subsequent analytical reaction. Examples of such elution reagent that can be used include nucleotidase-free pure water and low-salt buffer.

Next, the dispensing nozzle is moved above the chip remover 65 and the dispensing chip 42 is removed from the dispensing nozzle. Next, the pressurizing nozzle 12 connected to the arm 16 is moved above the nucleic acid capturing column 35 into which the solution obtained in the previous step has been discharged. Then, the pressurizing nozzle 12 is lowered so as to closely adhere to the nucleic acid capturing column 35 via a sealing member 36.

Next, the pressurizing pump 10 is operated such that the solution in the nucleic acid capturing column 35 is discharged. The thus discharged solution is discharged into a purified product container 28 on a purified product container rack 27 provided to the lower part of the elution unit 62. After the discharge of the solution in the provided nucleic acid capturing column 35, the pressurizing nozzle 12 is elevated and temporarily moved to the waiting position 68, and then it is stopped.

As a result of the above operations, a nucleic acid purification operation for a single specimen is completed.

In the first embodiment of the present invention, the configuration of the invention is described as follows. A solution containing nucleic acids and the like in a nucleic acid capturing column 35 is discharged into a closed channel, and at the same time, the air containing the mist of the solution containing nucleic acids and the like is released outside via a protection filter 51 that captures the mist. After the completion of the discharge of the solution containing nucleic acids and the like in the nucleic acid capturing column 35, the solution containing nucleic acids and the like in the closed channel is collected.

Thus, according to the first embodiment of the present invention, it is possible to realize a nucleic acid purification method and a nucleic acid purification instrument whereby it is possible to prevent dispersion of a mist that causes contamination upon discharge of a solution.

In addition, the above examples are described regarding the case in which a single specimen is treated. It is also possible to treat a plurality of specimens at once. In the case of a nucleic acid purification instrument 100 shown in FIG. 3, it is possible to simultaneously use 5 specimens at a maximum. In such case, in order to dispense a specimen, an adsorption reagent, a first washing reagent, a second washing reagent, and an elution reagent, a dispensing operation is repeatedly carried out for each specimen. Then, with the use of a plurality of necessary pumps, it is possible to simultaneously subject a plurality of nucleic acid capturing columns 35 to pressurization so as to allow each solution in each nucleic acid capturing column 35 to be discharged.

In addition, in order to avoid interference among airflows in a closed channel, it is necessary to provide a channel to each of a plurality of nucleic acid capturing columns 35. However, it is possible to use a common unit to allow the air in a closed channel to flow.

In addition, regarding the subsequent analytical reaction for purified nucleic acids, nucleic acid analysis involving the following can be applied: nucleic acid amplification, reverse transcription reactions, and nucleic acid elongation reactions, including PCR (Polymerase Chain Reaction), RT-PCR (Reverse Transcription-Polymerase Chain Reaction), LCR (Ligase Chain Reaction), SDA (Strand Displacement Amplification), NASBA (Nucleic Acid Sequence-Based Amplification), TMA (Transcription-Mediated Amplification), LAMP (Loop-mediated isothermal amplification), and ICAN (Isothermal and Chimeric primer-initiated Amplification of Nucleic acids); enzymatic reactions using restriction enzymes and the like; and electrophoresis.

Next, the second embodiment of the present invention is described with reference to FIG. 6. In the second embodiment of the present invention, a ventilation pump 90 that allows the air in a closed channel to flow is used and an aspiration fan 52 is omitted. The ventilation pump 90 is connected to a nucleic acid capturing column retention block 37 via a ventilation channel 91. The other constituent features are similar to those of the first embodiment, and thus detailed explanation thereof is herein omitted.

Figure 6:
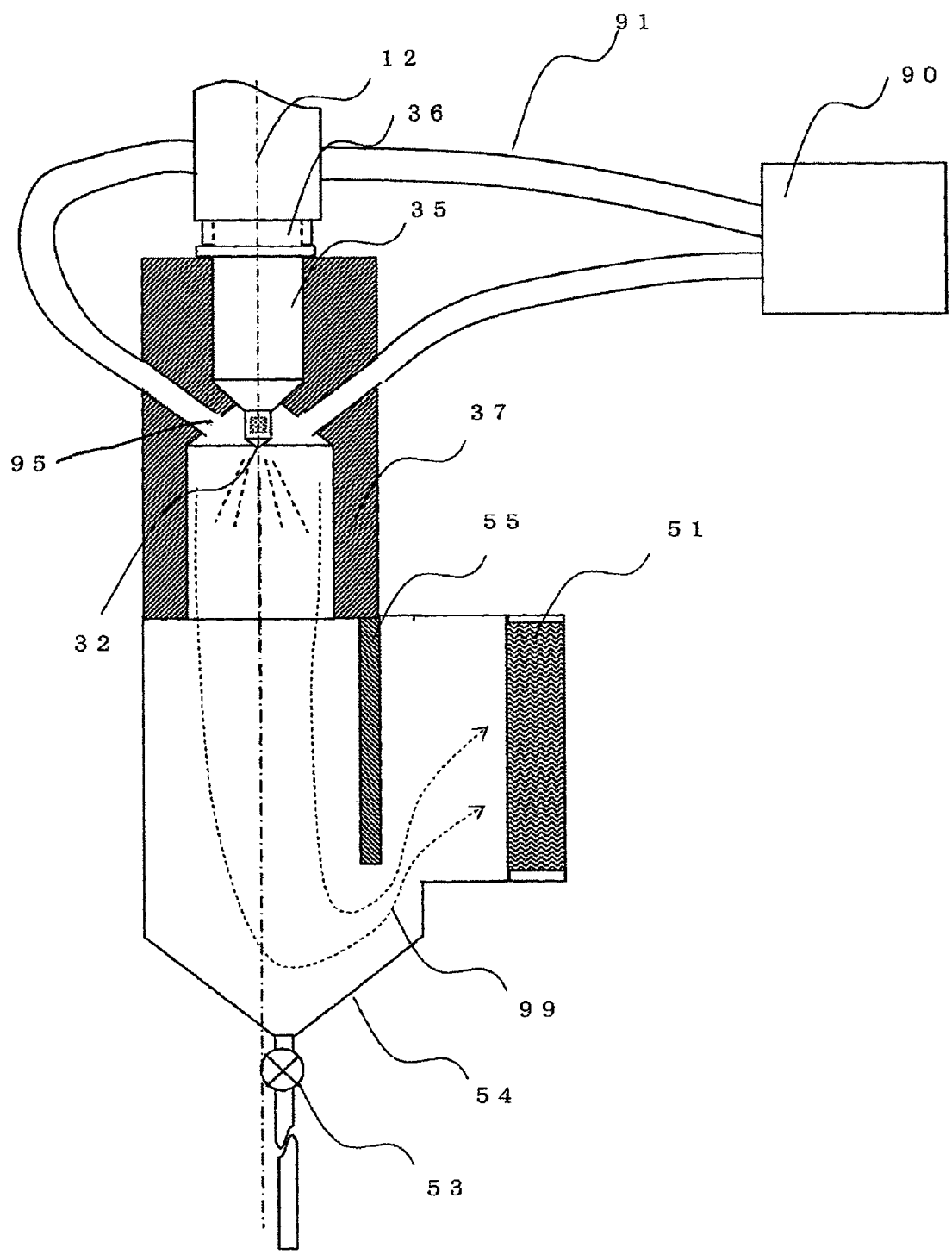
FIG. 6 shows a general structural diagram of a solution discharge channel in the second embodiment of the present invention.

In FIG. 6, a plurality of openings 95 for introducing the air that flows through a ventilation channel 91 into a closed channel are provided to the nucleic acid capturing column retention block 37. The formation of such openings 95 in the vicinity of a discharge opening 32 of a nucleic acid capturing column 35 allows the airflow to be directed toward the bottom part of a liquid receiving tank 54. Thus, the mist discharged from the discharge opening 32 is guided to a protection filter 51 and this makes it possible to prevent adherence of such mist to the nucleic acid capturing column 35 as a result of reverse flow.

Also, effects similar to those obtained in the first embodiment can be obtained in the second embodiment of the present invention.

In addition, it is also effective to use the aforementioned aspiration fan 52 described in the first embodiment in combination in the second embodiment of the present invention such that the aspiration fan 52 is allowed to function together with the ventilation pump 90.

In addition, in the second embodiment of the present invention, it is also possible to provide a heater in a ventilation channel 91. The mist flowing in the air is heated by heating the air flowing inside the nucleic acid capturing column retention block 37 so as to be evaporated in a short period of time. Thus, it can be expected that effects of reducing the volume of the mist that directly adheres to the protection filter 51 can be obtained.

In addition, as a portion to be heated with a heater, the nucleic acid capturing column retention block 37 can be heated. In such case, it is necessary to control temperature within a certain range in order to prevent nucleic acid purification steps from being affected.

Next, the third embodiment of the present invention is described with reference to FIG. 7. In the third embodiment of the present invention, a vacuum pump 93 that allows the air in a closed channel to flow is used and an aspiration fan 52 and a protection filter 51 are omitted. The vacuum pump 93 is connected to a closed channel via an open/close valve 94 and a vacuum buffer tank 92. The other constituent features are similar to those of the first embodiment and thus detailed explanation is herein omitted.

The open/close valve 94 is usually closed. In such state, aspiration is carried out such that a vacuum state in a vacuum buffer tank 92 is maintained at a certain level or to a greater degree. When a solution contained in a nucleic acid capturing column 35 is discharged into a liquid receiving tank 54, the open/close valve 94 is simultaneously opened such that the air in the closed channel is aspirated into the vacuum buffer tank 92. Accordingly, the air is allowed to flow and the mist in the closed channel is aspirated into the vacuum buffer tank 92.

The larger the capacity of the vacuum buffer tank 92 and the greater the ability of vacuum pump 93, the longer the time period during which the air is allowed to flow in the closed channel. Also, it is possible to allow the air to flow in an intermittent manner by opening the open/close valve 94 with appropriate timing in a repetitive manner while continuously operating the vacuum pump 93.

The mist contained in the vacuum buffer tank 92 can be separately subjected to disposal or the like.

Based on the third embodiment of the present invention as described above, the configuration of the invention is described as follows. The solution containing nucleic acids and the like is released into a closed channel from the nucleic acid capturing column 35, during which the air containing the mist of the solution containing nucleic acids and the like is aspirated into a vacuum buffer tank 92. Thereafter, the solution containing nucleic acids and the like in the closed channel is collected.

Thus, according to the third embodiment of the present invention, it is possible to realize a nucleic acid purification method and a nucleic acid purification instrument whereby it is possible to prevent dispersion of a mist that causes contamination upon discharge of a solution.

In addition, a ventilation unit used in a nucleic acid purification instrument is formed with a nucleic acid capturing column retention block 37, a liquid receiving tank (liquid accommodating tank) 54, a protection filter 51, an aspiration fan 52, and a partition board 55 shown in FIG. 1. The ventilation unit can be separately used as a part of a nucleic acid purification instrument.

Further, there is another ventilation unit formed with a nucleic acid capturing column retention block 37, a liquid receiving tank (liquid accommodating tank) 54, a protection filter 51, a ventilation pump 90, a partition board 55, and a ventilation channel 91 shown in FIG. 6.

Figure 7:
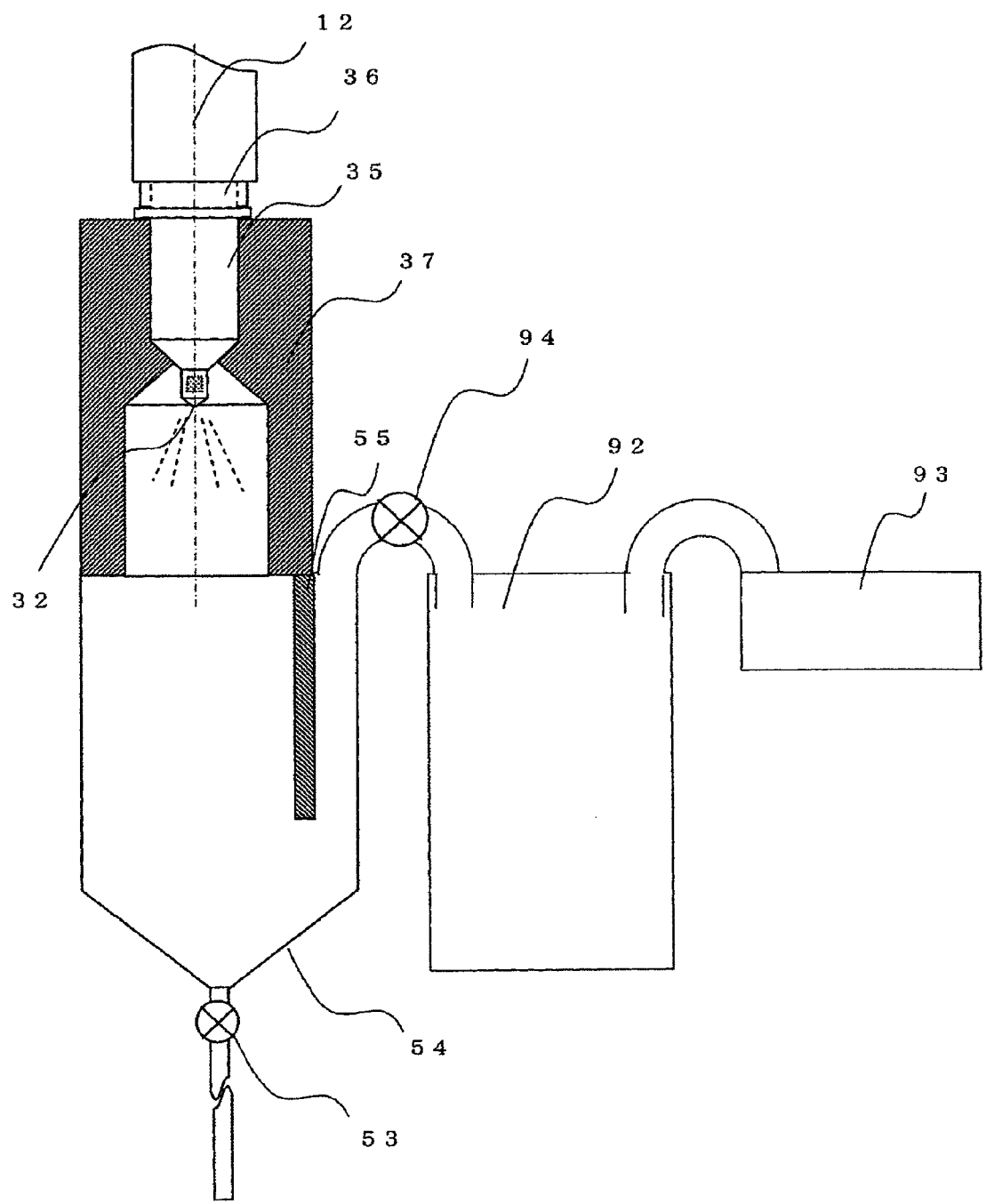
FIG. 7 shows a general structural diagram of a solution discharge channel in the third embodiment of the present invention.

Furthermore, there is another ventilation unit formed with a nucleic acid capturing column retention block 37, a liquid receiving tank (liquid accommodating tank) 54, a vacuum pump 93, a vacuum buffer tank 92, an open/close valve 94, and a partition board 55 shown in FIG. 7.

What is claimed is:

1. A nucleic acid purification instrument for purifying nucleic acids of interest from a liquid sample containing nucleic acids, comprising a nucleic acid capturing column having a nucleic-acid-adsorptive solid phase and a pressurizing unit for pressurizing a liquid supplied to the nucleic acid capturing column such that the liquid is allowed to pass through the nucleic-acid-adsorptive solid phase so as to be discharged from the nucleic acid capturing column, such instrument further comprising:

a liquid accommodating tank that is connected to a liquid discharge opening of the nucleic acid capturing column and accommodates the liquid discharged from the nucleic acid capturing column;

a capturing unit for capturing floating liquid components mixed with the air in the liquid accommodating tank, the capturing unit including a protection filter located on a sidewall of the liquid accumulating tank;

a ventilation unit for supplying air in a manner such that the floating liquid components mixed with air in the liquid accommodating tank flow toward the capturing unit; and a partition board located at a position facing the protection filter, wherein the partition board extends to a vertical direction to lead liquid discharged from the nucleic acid capturing column to the lower part of the liquid accommodating tank.

2. The nucleic acid purification instrument according to claim 1, wherein the ventilation unit is an aspiration fan for discharging the air that has passed through the protection filter outside the liquid accommodating tank, such fan being provided on the sidewall of the liquid accommodating tank.

3. The nucleic acid purification instrument according to claim 2, the air ventilated by the aspiration fan is allowed to flow starting from the vicinity of the liquid discharge opening of the nucleic acid capturing column to the bottom part of the liquid accommodating tank and then toward the protection filter.

4. The nucleic acid purification instrument according to claim 1, wherein a ventilation channel is formed in the vicinity of a connecting portion of the liquid accommodating tank and the liquid discharge opening of the nucleic acid capturing column, and the ventilation unit is a ventilation pump for ventilating air into the liquid accommodating tank via the ventilation channel.

5. The nucleic acid purification instrument according to claim 4, wherein the air ventilated by the ventilation pump is allowed to flow starting from the vicinity of the liquid discharge opening of the nucleic acid capturing column to the bottom part of the liquid accommodating tank and then toward the protection filter.

6. The nucleic acid purification instrument according to claim 4, wherein a heater for heating the air ventilated into the liquid accommodating tank by the ventilation pump is placed in the ventilation channel.

7. The nucleic acid purification instrument according to claim 1, wherein the capturing unit is a vacuum buffer tank that is connected to a sidewall of the liquid accommodating tank via an open/close valve, and the ventilation unit is a vacuum pump that is connected to the vacuum buffer tank.

8. The nucleic acid purification instrument according to claim 7, wherein the air ventilated by the vacuum pump via the vacuum buffer tank is allowed to flow starting from the vicinity of the liquid discharge opening of the nucleic acid capturing column to the bottom part of the liquid accommodating tank and then toward the vacuum buffer tank.

9. A nucleic acid purification method wherein nucleic acids of interest are purified from a liquid sample containing nucleic acids by pressurizing a liquid supplied to a nucleic acid capturing column having a nucleic-acid-adsorptive solid phase such that the liquid is allowed to pass through the nucleic-acid-adsorptive solid phase so as to be discharged from the nucleic acid capturing column, such method comprising the steps of:

providing the nucleic acid purification instrument of claim 1;

connecting the liquid accommodating tank for accommodating the liquid discharged from the nucleic acid capturing column to the liquid discharge opening of the nucleic acid capturing column;

pressurizing the liquid supplied to the nucleic acid capturing column such that the liquid is allowed to pass through the nucleic-acid-adsorptive solid phase so as to be discharged from the nucleic acid capturing column;

capturing the floating liquid components mixed with the air in the liquid accommodating tank so as to remove the liquid components floating with the air; and ventilating the air outside the liquid accommodating tank.

10. A ventilation unit used in a nucleic acid purification instrument for purifying nucleic acids of interest from a liquid sample containing nucleic acids with the use of a nucleic acid capturing column having a nucleic-acid-adsorptive solid phase, such ventilation unit comprising:

a liquid accommodating tank for accommodating a liquid discharged from the nucleic acid capturing column, such tank being connected to a liquid discharge opening of the nucleic acid capturing column;

a protection filter for capturing floating liquid components mixed with air in the liquid accommodating tank, such filter being located on a sidewall of the liquid accommodating tank;

an aspiration fan for discharging the air that has passed through the protection filter outside the liquid accommodating tank, such aspiration fan being located on a sidewall of the liquid accommodating tank; and a partition board for allowing the air ventilated by the aspiration fan to flow starting from the vicinity of the liquid discharge opening of the nucleic acid capturing column to the bottom part of the liquid accommodating tank and then toward the protection filter, such partition board being located at a position facing the protection filter in the liquid accommodating tank and extending to a vertical direction to lead liquid discharged from the nucleic acid capturing column to the lower level of the liquid accommodating tank.

11. A ventilation unit used in a nucleic acid purification instrument for purifying nucleic acids of interest from a liquid sample containing nucleic acids with the use of a nucleic acid capturing column having a nucleic-acid-adsorptive solid phase, such ventilation unit comprising:

a liquid accommodating tank for accommodating a liquid discharged from the nucleic acid capturing column, such tank being connected to a liquid discharge opening of the nucleic acid capturing column such that a ventilation channel is formed in the vicinity of a connecting portion of the tank and the liquid discharge opening of the nucleic acid capturing column;

a protection filter for capturing floating liquid components mixed with air in the liquid accommodating tank, such filter being located on a sidewall of the liquid accommodating tank;

a ventilation pump for ventilating the air into the liquid accommodating tank via the ventilation channel of the liquid accommodating tank; and a partition board for allowing air ventilated by the ventilation pump to flow starting from the vicinity of the liquid discharge opening of the nucleic acid capturing column to the bottom part of the liquid accommodating tank and then toward the protection filter, such partition board being located at a position facing the protection filter in the liquid accommodating tank and extending to a vertical direction to lead liquid discharged from the nucleic acid capturing column to the lower level of the liquid accommodating tank.

12. A ventilation unit used in a nucleic acid purification instrument for purifying nucleic acids of interest from a liquid sample containing nucleic acids with the use of a nucleic acid capturing column having a nucleic-acid-adsorptive solid phase, such ventilation unit comprising:

a liquid accommodating tank for accommodating the liquid discharged from the nucleic acid capturing column, such tank being connected to a liquid discharge opening of the nucleic acid capturing column;

a protection filter for capturing floating liquid components mixed with air in the liquid accommodating tank, such filter being located on a sidewall of the liquid accommodating tank;

a vacuum buffer tank that is connected to a sidewall of the liquid accommodating tank via an open/close valve;

a vacuum pump that is connected to the vacuum buffer tank; and a partition board for allowing air ventilated by the vacuum pump via the vacuum buffer tank to flow starting from the vicinity of the liquid discharge opening of the nucleic acid capturing column to the bottom part of the liquid accommodating tank and then toward the vacuum buffer tank, such partition board being located in the liquid accommodating tank and extending to a vertical direction to lead liquid discharged from the nucleic acid capturing column to the lower level of the liquid accommodating tank.

* * * * *

UNITED STATES PATENT AND TRADEMARK OFFICE
CERTIFICATE OF CORRECTION

PATENT NO. : 8,017,379 B2  Page 1 of 1
APPLICATION NO. : 12/175083
DATED : September 13, 2011
INVENTOR(S) : Yoshiyuki Shoji et al.

It is certified that error appears in the above-identified patent and that said Letters Patent is hereby corrected as shown below:

Title Page, Item (57) Abstract; has the below noted errors:

On line 2 "thai" should read --that--

On line 10 "tho" should read --the--

On line 13 "mi ihe" should read --in the--

On line 16 "bo" should read --be--

Signed and Sealed this
Thirty-first Day of July, 2012

David J. Kappos
*Director of the United States Patent and Trademark Office*

UNITED STATES PATENT AND TRADEMARK OFFICE
CERTIFICATE OF CORRECTION

PATENT NO.         : 8,017,379 B2
APPLICATION NO.    : 12/175083
DATED              : September 13, 2011
INVENTOR(S)        : Yoshiyuki Shoji It is certified that error appears in the above-identified patent and that said Letters Patent is hereby corrected as shown below:

Title Page, Item (75)
Yoshihiro Yamashita, reads "Hitahinaka (JP)" it should read -- Hitachinaka (JP) --
Toshinari Sakurai, reads "Hitahinaka (JP)" it should read -- Hitachinaka (JP) --
Hiroshi Umetsu, reads "Hitahinaka (JP)" it should read -- Hitachinaka (JP) --

Signed and Sealed this
Second Day of October, 2012

David J. Kappos
*Director of the United States Patent and Trademark Office*